US00PP16937P2

(12) United States Plant Patent
Kordes

(10) Patent No.: US PP16,937 P2
(45) Date of Patent: Aug. 1, 2006

(54) FLORIBUNDA ROSE PLANT NAMED 'KORGRETAUM'

(50) Latin Name: *Rosa hybrida*
Varietal Denomination: KORgretaum

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/071,751

(22) Filed: Mar. 2, 2005

(51) Int. Cl.
*A01H 5/00* (2006.01)

(52) U.S. Cl. ..... Plt./144

(58) Field of Classification Search ..... Plt./144
See application file for complete search history.

(56) References Cited

PUBLICATIONS

Gemman PBR Application ROS 2451 Apr. 5, 2004 W. Kordes' Söhne.

QZ (CPVO) Application 20041557 Aug. 19, 2004 W. Kordes' Söhne.

*Primary Examiner*—Kent Bell
*Assistant Examiner*—June Hwu

(57) ABSTRACT

A new and distinct variety of rose with abundant cream white flowers and glossy foliage with excellent disease resistance. It exhibits uniform upright and bushy growth. The new variety propagates well using traditional methods. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is 'KORgretaum'.

BACKGROUND OF THE INVENTION

The new variety of rose plant of the present invention originated from a controlled crossing in a breeding program of two distinct parents during the summer of 1992. The crossing was between 'Margaret Merrill', a non-patented rose and an un-named seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORgretaum'.

SUMMARY OF THE INVENTION

The new rose plant may be distinguished from its seed parent, 'Margaret Merrill', by the following combination of characteristics:

1. 'KORgretaum' has better disease resistance,
2. 'KORgretaum' has more petals, and
3. 'KORgretaum' has bushier growth.

The new rose plant may be distinguished from its pollen parent, an un-named seedling by the following combination of characteristics:

1. The flowers of 'KORgretaum' are white, while the flowers of the un-named seedling are pink,
2. the flowers of 'KORgretaum' are larger, and
3. the plant of 'KORgretaum' is larger.

The objective of the hybridization was to create a new and distinct rose plant with unique qualities, such as:

1. Vigorous, yet compact, uniform growth;
2. Abundant attractive, recurrent flowers;
3. Attractive and abundant foliage, and;
3. Resistance to diseases encountered in landscapes and gardens.

This combination of qualities is not present in prior rose cultivars. These objectives have been substantially achieved and in that distinguish 'KORgretaum' from all other varieties of which we are aware.

As part of a rose development program, Tim-Hermann Kordes germinated seeds from the aformentioned hybridization and conducted evaluations and observations on the resulting seedlings in a controlled environment in Offenseth-Sparrieshoop, Germany. The resulting seedlings exhibited distinctive physical and biological characteristics. The new rose plant 'KORgretaum' was selected in May, 1993 from the seedling beds to be asexually propagated for further evaluation. The first asexual propagation of 'KORgretaum' was done by budding to seedling understocks in July, 1993 at the W. Kordes Söhne Nursery in Offenseth-Sparrieshoop, Germany.

This initial and other subsequent propagations conducted in controlled environments show that the foregoing and all other characteristics of 'KORgretaum' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, and leaves of 'KORgretaum'. Specifically illustrated in SHEET ONE are open blooms and foliage of 'KORgretaum'.

DETAILED BOTANICAL DESCRIPTION

The following is a description of 'KORgretaum', as observed in its growth in September, 2004 in a nursery in Jackson County, Oreg. on plants of 1 year of age and in a nursery in Sparrieshoop, Germany on plants of 3 years of age. Color references are made using The Royal Horticultural Society (London, England) Colour Chart, 2001 except where common terms of color are used.

For a comparison, several physical characteristics of the rose variety 'KORbin', a non-patented rose are compared to 'KORgretaum' in Chart 1.

CHART 1

| | 'KORgretaum' | 'KORbin' |
|---|---|---|
| Disease resistance | Disease resistant | Susceptible to black spot and mildew. |
| Thorns | 8–10 thorns per 10 cm of stem. | Nearly thornless. |

Parents:

*Seed parent.*—'Margaret Merrill'.

*Pollen parent.*—An un-named seedling.

Classification:

*Botanical classification.*—*Rosa hybrida,* 'KORgretaum'.

*Commercial classification.*—Floribunda rose.

FLOWER AND FLOWER BUD

Blooming habit: Recurrent.

Flower bud:

*Size.*—Upon opening, 30–35 mm in length from base of receptacle to end of bud.

*Bud form.*—Pointed ovoid.

*Bud color.*—As sepals first unfold, bud color is White Group 155C with intonations of Yellow-Green Group 149C. During cool weather, bud also expresses intonations of Greyed-Red Group 179A. When ¼ open, the upper surface of petals is White Group 157D with similar, but less pronounced intonations. Guard petals are Yellow-Green Group 149D with some expression of Greyed-Red Group 179A.

*Sepals.*—Size: Average 22–30 mm long×6–8 mm wide. Shape: Weak foliaceous appendages on three of the five sepals. Transitions to a narrow, linear point. Base is flat at union with receptacle. Quantity: Five. Surface texture: Upper and lower surfaces moderately pubescent. Color: Upper surface Green Group 138B. Lower surface Green Group 138A.

*Receptacle.*—Surface: Smooth. Color: Green Group 138B. Shape: Pear shaped. Size: 8–10 mm (h)×6–8 mm (w).

*Peduncle.*—Surface: Smooth. Length: 35–50 mm average length. Diameter: 1.5 mm average diameter. Color: Green Group 138A. Intonations of Greyed-Red Group 181A abundant on juvenile peduncles. Decreasing as tissue matures. Strength: Strong. Borne: Multiple flower buds per stem, generally 4 to 10.

Flower bloom:

*Fragrance.*—Light sweet fragrance.

*Duration.*—Individual blooms have a duration of 4–6 days on the plant. As a cut flower, the inflorescence lasts 7–8 days.

*Size.*—Individual flowers with flower diameter of 50–65 mm when open.

*Form.*—Shape of flower when viewed from the side: Upon opening, upper part: Flat to flattened convex. Upon opening, lower part: Flattened convex. Open flower, upper part: Flat. Open flower, lower part: Concave.

Color:

*Upon opening, petals.*—Outermost petals: Outer Side: Green-White Group 157D. Inner Side: Green-White Group 157D. Innermost petals: Outer Side: Green Group 157C. Inner Side: Lower half of petal Green-White Group 157D. Upper half of petal Orange-White Group 159D.

*Upon opening, basal petal spots.*—Basal petal spot, outermost petals: Outer Side: Yellow Group 2D. Inner Side: Yellow Group 2D. Basal petal spot, innermost petals: Outer Side: Yellow Group 1D. Inner Side: Point of attachment Green-White Group 157C. This transitions to Green-White Group 157A, then to Yellow Group 3D above.

*After opening, petals.*—Outermost petals: Outer Side: White Group 155C. Inner Side: White Group 155C. Innermost petals: Outer Side: White Group 155C. Inner Side: White Group 155C.

*After opening, basal petal spots.*—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D. Variegations: None.

General tonality: On open flower, Outermost portion of flower White Group 155C. Towards center of bloom, Orange-White Group. No change in the general tonality at the end of the $5^{th}$ day. Afterwards, general tonality is White Group 155C.

Petals:

*Petal count.*—Approximately 45–50 petals under normal conditions.

*Petal reflex.*—Inner petals not reflexed. Some of outer petals reflex slightly.

*Petal edge.*—Variable. Some petal edges with a point in center, others with a notch.

*Petal shape.*—Rounded to deltoid.

*Petal size.*—Variable. 24–30 mm long; 16–30 mm wide.

*Thickness.*—Average thickness.

*Petal arrangement.*—Generally informal.

*Petaloids.*—Present. Commonly 10–12 per flower. Petaloids are 15 mm long and 8–12 mm wide. Color of upper half of inner side is Orange-White Group 159D. Color of lower half of inner side is Yellow Group 1D. Color of upper half of outer side is Orange-White Group 159D. Color of lower half of outer side is Yellow Group 1D. Surface texture is smooth. Shape is elliptic.

Reproductive organs:

*Pistils.*—Average 50 in number per bloom. Stigmas: Location: Superior in location to anthers. Color: Greyed-Green Group 196C. Styles: Length: 8–10 mm long. Color: Green-White Group 157B. Immediately below stigma, a narrow band of Greyed-Red Group 183C. Below this band, color transitions to Green-White Group 157D.

*Stamens.*—Quantity: Approximately 50. Anthers: Size: 2–3 mm long. Color: Yellow-Orange Group 16C. Pollen: Average abundance. Color: Yellow-Orange Group 16C. Filaments: Color: Yellow-Green Group 151D. Length: 3–4 mm.

THE PLANT

Plant growth: Vigorous. Upright to bushy. When grown as a budded nursery plant the plant height is 80–120 cm and the plant width is 60–100 cm.

Stems:

*Stem color.*—Young wood: Green Group 138A. Juvenile wood with intonations of Greyed-Red Group 179A. Older wood: Green Group 138A.

*Stem surface.*—Young wood: Smooth. Older wood: Smooth to rough.

Prickles: Present.

*Incidence.*—8–10 per 10 cm of stem.

*Size.*—Average length: 11–13 mm.

*Color.*—Distal end of juvenile thorns Greyed-Red Group 179A. Basal end of juvenile thorns Greyed-Red Group 179C. Mature thorns are Greyed-Orange Group 174D.

*Shape.*—Deeply concave.

Leaves and leaflets: Normally 5 leaflets on normal leaves in middle of the stem.

*Leaf size.*—90–110 mm (l)×65–75 mm (w).

*Quantity.*—Abundant.

*Texture.*—Glossy. Thick.

*Color, mature foliage.*—Upper Leaf Surface: Green Group 139A. Lower Leaf Surface: Green Group 138A.

*Color, juvenile foliage.*—Upper Leaf Surface: Green Group 138A. With intonations of Greyed-Purple Group 187D. As leaf matures, intonation disappears. Lower Leaf Surface: Green Group 138A.

Stipules:

*Size.*—15–17 mm (l) — 4–5 mm (w).

*Stipule color.*—Green Group 138A. Juvenile growth with intonations of Greyed-Purple Group 187D.

*Presence of stipitate glands.*—Present on margins.

*Margins.*—Bearded. With stipitate glands in limited numbers.

Petiole:

*Length.*—10–15 mm.

*Diameter.*—1.5 mm.

*Petiole color.*—Green Group 138A. Juvenile growth with intonations of 187D.

*Prickles.*—A few small prickles underneath.

*Stipitate glands.*—Limited numbers of stipitate glands on margins.

Petiole rachis:

*Length.*—10–12 mm.

*Diameter.*—1.5 mm.

*Petiole color.*—Green Group 138A. Juvenile growth with intonations of 187D.

*Prickles.*—A few small prickles underneath.

*Stipitate glands.*—Limited numbers of stipitate glands on margins.

Leaflets:

*Size.*—Average size of the terminal leaflet is 40 mm(l)× 28–30 mm(w).

*Shape.*—Pointed oval. Leaflet base: Rounded. Leaflet apex: Acute.

*Margins.*—Serrated.

*Texture.*—Glossy. Thick.

Hips/seed formation: None observed.

Winter hardiness observation: To date, the new variety has been grown successfully in Zone 5.

Disease resistance: Excellent resistance to black spot, powdery mildew, and rust diseases under normal growing conditions.

I claim:

1. A new and distinct variety of rose plant characterized by the following combination of characteristics:

(a) forms abundant, attractive cream white flowers;

(b) exhibits uniform upright and bushy growth habit;

(c) propagates well using traditional methods, and;

(d) exhibits excellent resistance to disease under normal growing conditions;

substantially as herein illustrated and described.

* * * * *

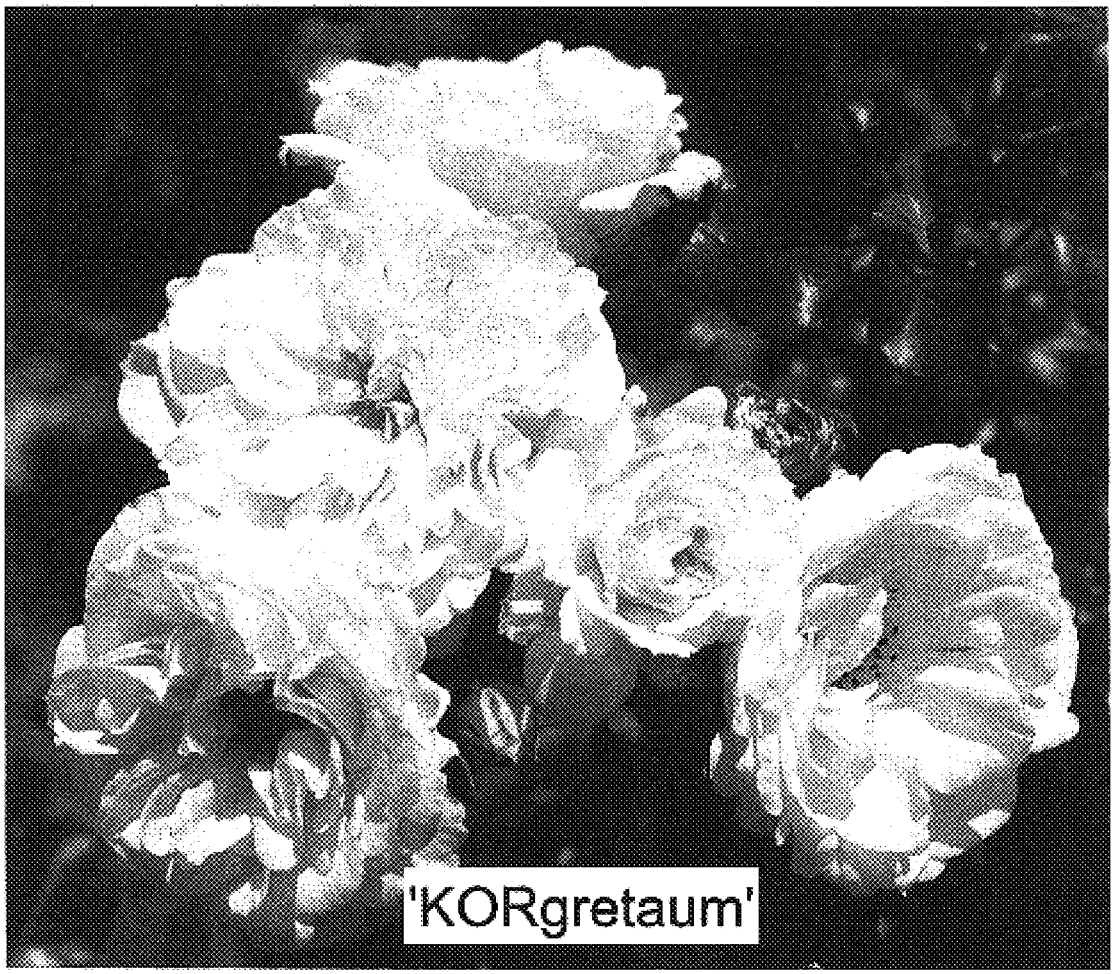
'KORgretaum'